(12) United States Patent
Abdelghani

(10) Patent No.: US 11,780,789 B2
(45) Date of Patent: Oct. 10, 2023

(54) BUTADIENE HEAT INTEGRATION PROCESS

(71) Applicant: SABIC Global Technologies B.V., Bergen op Zoom (NL)

(72) Inventor: Mohamed Sabri Abdelghani, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/786,813

(22) PCT Filed: Nov. 5, 2020

(86) PCT No.: PCT/IB2020/060427
§ 371 (c)(1),
(2) Date: Jun. 17, 2022

(87) PCT Pub. No.: WO2021/123950
PCT Pub. Date: Jun. 24, 2021

(65) Prior Publication Data
US 2023/0030123 A1 Feb. 2, 2023

Related U.S. Application Data

(60) Provisional application No. 62/950,785, filed on Dec. 19, 2019.

(51) Int. Cl.
*C07C 7/00* (2006.01)
*C07C 7/04* (2006.01)

(52) U.S. Cl.
CPC ............... *C07C 7/005* (2013.01); *C07C 7/04* (2013.01)

(58) Field of Classification Search
CPC combination set(s) only.
See application file for complete search history.

(56) References Cited

U.S. PATENT DOCUMENTS

| | | |
|---|---|---|
| 4,162,198 A | 7/1979 | Stockburger et al. |
| 5,242,550 A | 9/1993 | Asselineau et al. |
| 8,252,150 B1 | 8/2012 | Hsu et al. |
| 9,296,667 B2 | 3/2016 | Schwint et al. |
| 2018/0273446 A1 | 9/2018 | Ignat et al. |

FOREIGN PATENT DOCUMENTS

WO    WO 2014/070447    5/2014

OTHER PUBLICATIONS

International Search Report and Written Opinion issued in Corresponding PCT Application No. PCT/IB2020/060427, dated Feb. 1, 2021.

*Primary Examiner* — Thuan D Dang
(74) *Attorney, Agent, or Firm* — Norton Rose Fulbright US LLP

(57) ABSTRACT

Systems and methods for separating a mixture comprising $C_4$ hydrocarbons and a solvent have been disclosed. The mixture is produced as a bottom stream of a rectifier column. The mixture is processed in at least two heating and flash-evaporating cycles to remove at least some $C_4$ hydrocarbons as vapor streams. The resulted liquid stream is further degassed in a degasser column to produce a recycle vapor stream and a lean solvent stream.

20 Claims, 5 Drawing Sheets

BUTADIENE HEAT INTEGRATION PROCESS

CROSS REFERENCE TO RELATED APPLICATIONS

This application is a national phase under 35 U.S.C. § 371 of International Application No. PCT/IB2020/060427, filed Nov. 5, 2020, which claims the benefit of priority to U.S. Provisional Patent Application No. 62/950,785, filed Dec. 19, 2019, the entire contents of each of which are hereby incorporated by reference in their entirety.

FIELD OF INVENTION

The present invention generally relates to systems and methods for separating 1,3-butadiene from a hydrocarbon mixture. More specifically, the present invention relates to a 1,3-butadiene separation system and process that includes optimized heat integration for recovering a hydrocarbon from a solvent that is used in an extractive distillation process.

BACKGROUND OF THE INVENTION 1,3-butadiene is a valuable chemical that can be used as a raw material in many chemical production processes. For instance, 1,3-butadiene can be used to produce polybutadiene, which is the main component of synthetic rubber. Furthermore, butadiene can be used for making adiponitrile, a nylon intermediate, via a hydrocyanation process.

Conventionally, 1,3-butadiene is produced via various processes including extraction from $C_4$ raffinate of steam crackers, dehydrogenation of n-butane, and dehydrogenation of butenes. In the process of extractive distillation of $C_4$ raffinate from steam crackers, a 1,3-butadiene containing stream from an extractive distillation column is separated in a rectifier column; specifically, 1,3-butadiene is separated from a solvent used in the extractive distillation column. The solvent leaving the bottom of the rectifier column, which contains dissolved $C_4$ hydrocarbons, is partially degassed before reaching the degasser, and in the degasser column is completely degassed to produce lean solvent free of hydrocarbons from the bottom and a vapor deposition stream from the overhead comprising butadiene-rich $C_4$ hydrocarbons in addition to a side-draw stream for acetylene removal. The hot lean solvent from the degasser column is used as the heating medium for a reboiler of the rectifier column through a set of heat exchangers that exchange heat between hot lean solvent against the cold solvent containing hydrocarbons. The heat exchangers act as the column reboiler so as to optimize heat recovery. When the rich solvent containing $C_4$ hydrocarbons is flowed from the bottom of the rectifier to the reboiler column, the heat exchangers of the reboiler may be subject to high risk of fouling, due to high concentration of hydrocarbons in the rich solvent that is being heated with high temperature of degassed lean solvent from degasser, thereby reducing the efficiency and increasing the operating cost for producing 1,3-butadiene. Furthermore, the degasser, which operates at lower pressure than the rectifier column, produces a large volume of vapor stream, which is compressed and is recycled back to the rectifier column. Thus, the large volume of vapor stream can result in high energy consumption for the compressing step, which accounts for about 60% of the total electric load of the plant, thereby increasing the operational cost.

Overall, while systems and methods for separating 1,3-butadiene from a $C_4$ mixture exist, the need for improvements in this field persists in light of at least aforementioned drawbacks for the conventional systems and methods.

BRIEF SUMMARY OF THE INVENTION

A solution to at least the above-mentioned problems associated with the systems and methods for separating 1,3-butadiene from a $C_4$ hydrocarbon mixture has been discovered. The solution resides in a system and a method for recovering hydrocarbon from a solvent that is used in extractive distillation of the $C_4$ hydrocarbon mixture. The recovery process of the solvent can be implemented in a 1,3-butadiene separation system. The method and system include optimized heat integration for the solvent recovery process, which includes at least flash-evaporating a bottom stream from a rectifier column twice before the bottom stream is fed into the degasser column. This can be beneficial for at least reducing the vapor stream produced from the degasser overhead, thereby reducing the energy consumption for the compressor configured to compress the vapor stream from the degasser column. Furthermore, the multiple flash-evaporating steps can reduce the concentration of $C_4$ hydrocarbons in the partially degassed solvent from the rectifier column, resulting in reduced fouling risk in the heat exchange units used to heat the bottom stream from the rectifier column when the lean solvent stream is used as a heating medium. Additionally, the cold lean solvent leaving the rectifier heat exchangers is heated back against the final hot partially degassed solvent in a heat exchanger to adjust its temperature and also to cool down the degassed solvent temperature before the partially degassed solvent enters the degasser. The re-heated lean solvent exiting this heat exchanger can therefore be further utilized as a heating medium to provide heat for downstream units, including a 1,3-butadiene refining column, optionally a propyne column, and feed vaporizer for a main washer column, further optimizing the heat integration of the process of separating 1,3-butadiene. The partially degassed solvent that is cooled by exchanging heat with cooled lean solvent stream is fed to the degasser at the desired temperature allowing good control of process parameters of the degasser column. Therefore, the systems and methods of the present invention provide a technical solution to at least some of the problems associated with the conventional systems and methods for 1,3-butadiene separation as mentioned above.

Embodiments of the invention include a method of separating a mixture comprising (1) $C_4$ hydrocarbons and (2) a solvent of the $C_4$ hydrocarbons. The method comprises separating the mixture of $C_4$ hydrocarbons in a rectifier column to produce a top stream comprising at least some $C_4$ hydrocarbons and a bottom stream comprising (a) primarily the solvent and (b) at least some $C_4$ hydrocarbons. The method comprises heating the bottom stream in a first heat exchange unit to form a first heated bottom stream at a first temperature. The method comprises flash-evaporating the first heated bottom stream to separate at least some $C_4$ hydrocarbons from the first heated bottom stream and thereby form a first degassed bottom stream. The method comprises heating the first degassed bottom stream in a second heat exchange unit and/or a third heat exchange unit to form a second heated bottom stream at a second temperature. The method comprises flash-evaporating the second heated bottom stream to separate at least some $C_4$ hydrocarbons from the second heated bottom stream and thereby form a second degassed bottom stream. The method further comprises feeding the second degassed bottom stream as a degasser feed stream to a degasser column to further remove remaining $C_4$ hydrocarbons from the solvent. The method further still comprises removing $C_4$ hydrocarbons from the degasser feed stream in the degasser column to produce a degasser top stream comprising the $C_4$ hydrocarbons in vapor phase, and a lean solvent stream comprising primarily the solvent.

Embodiments of the invention include a method of separating a mixture comprising (1) $C_4$ hydrocarbons and (2) a solvent of the $C_4$ hydrocarbons. The method comprises separating the mixture of $C_4$ hydrocarbons in a rectifier column to produce a top stream comprising at least some $C_4$ hydrocarbons and a bottom stream comprising (a) primarily the solvent and (b) at least some $C_4$ hydrocarbons. The method comprises heating the bottom stream in a first heat exchange unit against a second hot lean solvent stream to form a first heated bottom stream at a first temperature and a cooled lean solvent stream. The method comprises flash-evaporating the first heated bottom stream to separate at least some $C_4$ hydrocarbons from the first heated bottom stream and thereby form a first degassed bottom stream. The method comprises heating the first degassed bottom stream sequentially in a third heat exchange unit against steam and in a second heat exchange unit against a first hot lean solvent stream to form a second heated bottom stream at a second temperature and the second hot lean solvent stream. The method comprises flash-evaporating the second heated bottom stream to separate at least some $C_4$ hydrocarbons from the second heated bottom stream and thereby form a second degassed bottom stream. The method further comprises feeding the second degassed bottom stream as a degasser feed stream to a degasser column to further remove $C_4$ hydrocarbons from the solvent. The method further still comprises removing $C_4$ hydrocarbons from the degasser feed stream in the degasser column to produce a degasser top stream comprising the $C_4$ hydrocarbons in vapor phase, and a lean solvent stream comprising primarily the solvent. The method further comprises compressing the degasser top stream to form a compressed recycle stream. The method further still comprises flowing the compressed recycle stream to the rectifier column.

Embodiments of the invention include a method of separating a mixture comprising (1) $C_4$ hydrocarbons and (2) a solvent for the $C_4$ hydrocarbons. The method comprises separating the mixture of $C_4$ hydrocarbons in a rectifier column to produce a top stream comprising at least some $C_4$ hydrocarbons and a bottom stream comprising (a) primarily the solvent and (b) at least some $C_4$ hydrocarbons. The method comprises heating the bottom stream against a second hot lean solvent stream in a first heat exchange unit to form a first heated bottom stream at a first temperature and a cooled lean solvent. The method comprises flash-evaporating the first heated bottom stream to separate at least some $C_4$ hydrocarbons from the first heated bottom stream and thereby form a first degassed bottom stream. The method comprises heating the first degassed bottom stream in a second heat exchange unit against a first hot lean solvent stream to form a second heated bottom stream at a second temperature and the second hot lean solvent stream. The method comprises flash-evaporating the second heated bottom stream to separate at least some $C_4$ hydrocarbons from the second heated bottom stream and thereby form a second degassed bottom stream. The method comprises heating the second degassed bottom stream in a third heat exchange unit against low pressure steam to form a third heated bottom stream at a third temperature The method comprises flash-evaporating the third heated bottom stream to separate at least some $C_4$ hydrocarbons from the third heated bottom stream and thereby form a third degassed bottom stream. The method further comprises cooling, in a third heat exchange unit, the third degassed stream against the cooled lean solvent stream to form a cooled degassed stream to a feed temperature and heat the cooled lean solvent to form heated lean solvent stream. The method further comprises feeding the cooled third degassed bottom stream as a degasser feed stream to a degasser column. The method further still comprises removing substantially all remaining $C_4$ hydrocarbons from the degasser feed stream in the degasser column to produce a degasser top stream comprising the $C_4$ hydrocarbons in vapor phase, and the first hot lean solvent stream comprising primarily the solvent. The method further comprises compressing the degasser top stream to form a compressed recycle stream. The method further still comprises flowing the compressed recycle stream to the rectifier column.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

In the context of the present invention, at least twenty embodiments are now described.

Embodiment 1 is a method of separating a mixture containing (1) $C_4$ hydrocarbons and (2) a solvent. The method includes the steps of separating the mixture in a rectifier column to produce a top stream containing at least some $C_4$ hydrocarbons and a bottom stream containing (a) primarily the solvent and (b) at least some $C_4$ hydrocarbons; heating the bottom stream in a first heat exchange unit to form a first heated bottom stream at a first temperature; flash-evaporating the first heated bottom stream to separate at least some $C_4$ hydrocarbons from the first heated bottom stream to form a first degassed bottom stream; heating the first degassed bottom stream in a second heat exchange unit to form a second heated bottom stream at a second temperature; flash-evaporating the second heated bottom stream to separate at least some $C_4$ hydrocarbons from the second heated bottom stream to form a second degassed bottom stream; feeding at least a portion of the second degassed bottom stream as a degasser feed stream to a degasser column to further remove $C_4$ hydrocarbons from the solvent; and removing at least some $C_4$ hydrocarbons from the degasser feed stream in the degasser column to produce a degasser top stream containing the $C_4$ hydrocarbons in vapor phase, and a first hot lean solvent stream containing primarily the solvent. Embodiment 2 is the method of embodiment 1, further including, prior to the step of flash-evaporating the second heated bottom stream, heating the first degassed bottom stream in an additional heat exchange unit installed up stream or downstream to the second heat exchange unit. Embodiment 3 is the method of embodiment 2, wherein the additional heat exchange unit is operated with a low pressure steam as a heating medium. Embodiment 4 is the method of any of embodiments 1 to 3, further including the step of compressing the degasser top stream to form a compressed recycle stream; and flowing the compressed recycle stream to the rectifier column. Embodiment 5 is the method of embodiment 4, wherein the compressing is conducted using a compressor or a multiphase pump. Embodiment 6 is the method of any of embodiments 1 to 5, further including, prior to the feeding step, heating the second degassed bottom stream in a third heat exchange unit to form a third heated bottom stream at a third temperature; flash-evaporating the third heated bottom stream to separate at least some $C_4$ hydrocarbons from the third heated bottom stream to form a third degassed bottom stream; and feeding the third degassed bottom stream as a degasser feed stream to the degasser column configured to further remove $C_4$ hydrocarbons from the solvent. Embodiment 7 is the method of embodiment 6, wherein the third exchange unit is operated using low pressure steam as a heating medium. Embodiment 8 is the method of any of embodiments 6 and 7, wherein the flash-evaporating of the third heated bottom stream further produces a third vapor stream containing primarily the $C_4$ hydrocarbons, and the method further contains flowing the third vapor stream to the rectifier column. Embodiment 9 is the method of any of embodiments 1 to 8, wherein the first hot lean solvent stream is flowed into the first heat exchange unit and/or the second heat exchange unit as a heating medium to form a second hot lean solvent stream. Embodiment 10 is the method of embodiment 9, further including, prior to feeding the degasser feed stream to the degasser, cooling, in a fourth heat exchanger, the degasser feed stream with the cooled lean solvent stream as a cooling medium to form a cooled degasser feed stream and a heated lean solvent stream. Embodiment 11 is the method of embodiment 10, wherein the heated lean solvent stream is used as a heating medium to heat a reboiler of a 1,3-butadiene refining column configured to purify a crude 1,3-butadiene stream, and optionally a reboiler of a propyne refining column configured to separate propyne from a hydrocarbon mixture. Embodiment 12 is the method of embodiment 11, wherein the heated lean solvent stream is used as a heating medium to heat the reboiler of the propyne refining column and the reboiler of the 1,3-butadiene refining column in series. Embodiment 13 is the method of any of embodiments 10 to 12, wherein the heated lean solvent stream is used as a heating medium to heat a reboiler of a 1,3-butadiene refining column and a feed vaporizer configured to vaporize $C_4$ hydrocarbon feed for an extractive distillation column. Embodiment 14 is the method of embodiment 13, wherein the extractive distillation column is configured to separate the vaporized $C_4$ hydrocarbon feed to produce the mixture of $C_4$ hydrocarbons. Embodiment 15 is the method of any of embodiments 1 to 14, wherein the flash-evaporating of the first heated bottom stream further produces a first vapor stream containing primarily the $C_4$ hydrocarbons, and the flash-evaporating of the second heated bottom stream further produces a second vapor stream containing primarily the $C_4$ hydrocarbons, wherein the first vapor stream and the second vapor stream are flowed to the rectifier column. Embodiment 16 is the method of any of embodiments 1 to 15, wherein the $C_4$ hydrocarbons contain 1-butene, 2-butene, n-butane, isobutane, isobutene, 1,3-butadiene, 1,2-butadiene, cis and trans butene isomers, $C_4$ acetylenes, propyne, or combinations thereof. Embodiment 17 is the method of any of embodiments 1 to 16, wherein the removing at least some $C_4$ hydrocarbons from the degasser feed stream further produces a side stream containing $C_4$ acetylene. Embodiment 18 is the method of embodiment 17, wherein the side stream is further separated in an acetylene washer column to produce an acetylene stream containing less than 30 wt. % $C_4$ acetylene. Embodiment 19 is the method of any of embodiments 1 to 18, wherein the solvent contains n-methyl-2-pyrrolidone, dimethyl formamide, or acetonitrile. Embodiment 20 is the method of any of embodiments 1 to 19, wherein the first hot lean solvent stream contains less than 0.01 wt. % $C_4$ hydrocarbons.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, 1,3-butadiene is separated in a system that includes an extractive distillation column, a rectifier column, an after washer column, and a degasser column. A lean solvent stream from the degasser column is used as a heating medium for the reboiler of the rectifier column and a vapor stream from the degasser column is compressed and recycled back to the rectifier column. However, $C_4$ hydrocarbons in a feed stream of the degasser column are not sufficiently removed by the single degassing step. The high hydrocarbon content of the bottom stream from the rectifier bottom can significantly increase the risk of fouling in the heat exchange units when heating the bottom stream of the rectifier column that is rich in hydrocarbons against the hot lean solvent from the degasser column. Furthermore, the single degassing step also results in a large amount of hydrocarbons vapor stream produced in the degasser column. Thus, the compressing of the vapor stream in a recycle loop is highly energy intensive. The present invention provides a solution to at least some of the problems. The solution is premised on a method of separating a mixture of $C_4$ hydrocarbons from a solvent that includes multiple heating and flash-evaporating steps for the bottom stream from the rectifier column before it is fed into the degasser column. Thus, the disclosed method is capable of reducing $C_4$ hydrocarbon content in the solvent produced from the rectifier bottom, containing high concentration of hydrocarbons, Before heating the solvent to high temperatures, it is partially degassed at lower temperatures first and further degassed at higher temperatures at lower hydrocarbon concentrations before it is fed to the degasser column, thereby reducing fouling risk in the heat exchange unit(s) when the lean solvent stream is used as a heating medium. Additionally, the multiple heating and flash-evaporating steps can reduce the amount of vapor stream produced in the degasser column, resulting in reduced energy consumption for compressing the vapor stream from the degasser column. Moreover, after heating the reboiler of the rectifier column, the lean solvent can be heated back in a heat exchanger against the hot degassed solvent such that it can be further used for providing heat for one or more downstream units, further optimizing the heat integration for the system. The present invention can also allow for replacement of the compressor with a multiphase pump that can pump a mixture of vapor and liquid mixture from degasser pressure to rectifier column pressure due to lower degasser overhead flow rate, resulting in reduced energy consumption and capital cost. These and other non-limiting aspects of the present invention are discussed in further detail in the following sections.

A. System for Separating 1,3-butadiene from a Hydrocarbon Mixture

Figure 1A:
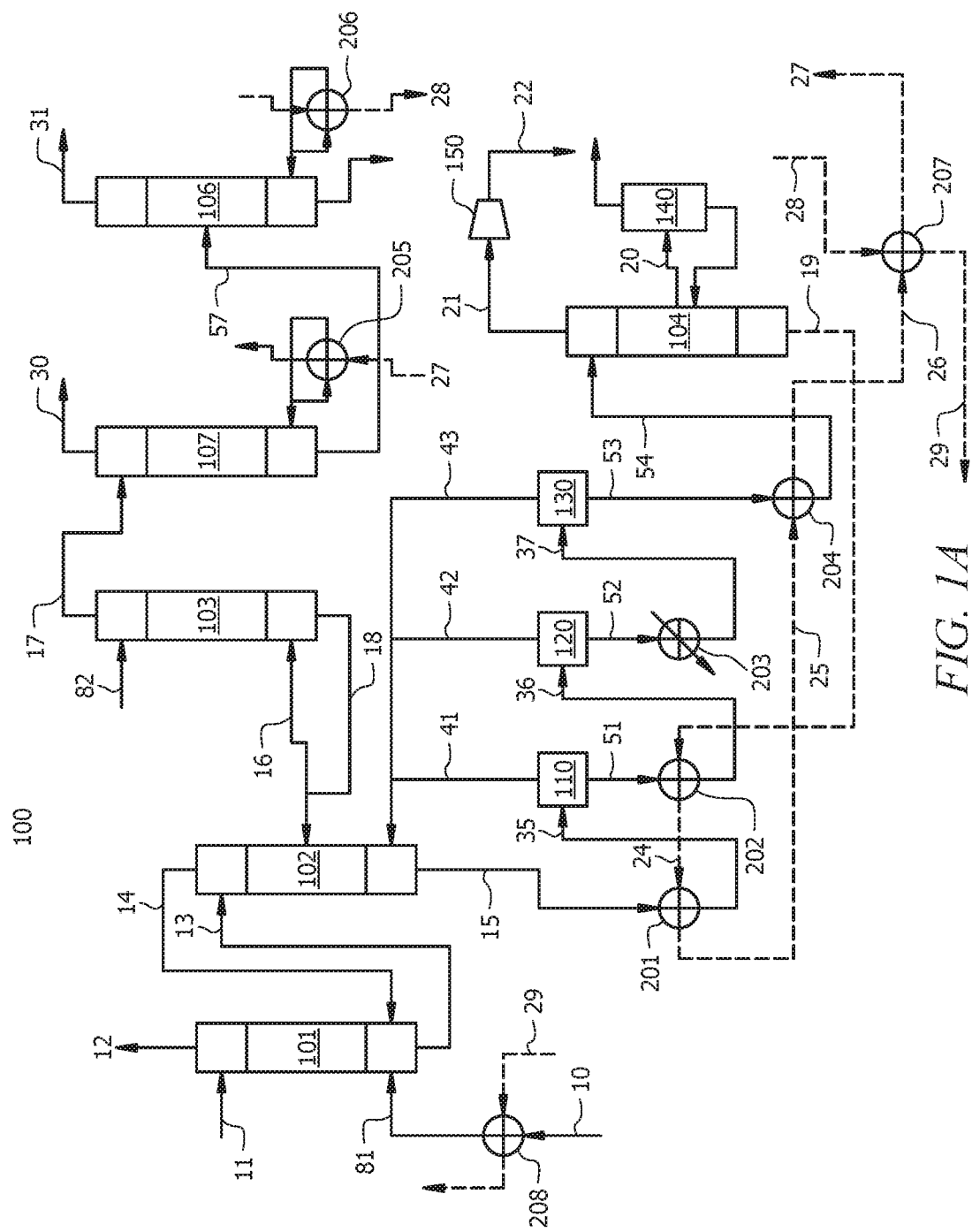
FIGS. 1A-1C show schematic diagrams of systems for separating 1,3-butadiene from a mixture of $C_4$ hydrocarbons, according to embodiments of the invention.

In embodiments of the invention, the system for separating $C_4$ hydrocarbons includes a main washer column (e.g., an extractive distillation column), a rectifier column, an after washer column, and a degasser column. The system is capable of reducing the fouling risk in the heat exchange units for heating the bottom stream of the rectifier column and reducing the energy consumption for producing 1,3-butadiene. With reference to FIG. 1A, a schematic diagram is shown for system 100, which is used for separating $C_4$ hydrocarbons and producing 1,3-butadiene with improved efficiency and reduced energy consumption compared to conventional systems.

According to embodiments of the invention, system 100 comprises main washer column 101. Main washer column 101 can include an extractive distillation column configured to separate $C_4$ hydrocarbon feed stream 81 with a solvent of first solvent stream 11 to produce first overhead stream 12 comprising 1-butene, 2-butene, isobutylene, isobutane, n-butane, or combinations thereof and first bottom stream 13 comprising a mixture of $C_4$ hydrocarbons and the solvent. The mixture of $C_4$ hydrocarbons of first bottom stream 13 may comprise 1,3-butadiene. The mixture of $C_4$ hydrocarbons can further comprise $C_4$ hydrocarbons other than 1,3-butadiene. In embodiments of the invention, the solvent comprises N-Methyl-1-2-Pyrrolidone (NMP). The solvent may further comprise 8-10 wt. % water, preferably about 8.3 wt. % water. The $C_4$ hydrocarbons may include 1-butene, 2-butene, n-butane, isobutane, isobutylene, acetylene, 1,3-butadiene, 1,2-butadiene, cis and trans butene isomers, or combinations thereof.

According to embodiments of the invention, a bottom outlet of main washer column 101 is in fluid communication with rectifier column 102 such that first bottom stream 13 flows from main washer column 101 to rectifier column 102. In embodiments of the invention, rectifier column 102 is configured to separate first bottom stream 13 to form top stream 14 comprising at least some $C_4$ hydrocarbons and bottom stream 15 comprising primarily the solvent and some $C_4$ hydrocarbons. $C_4$ hydrocarbons in both top stream 14 and bottom stream 15 include 1,3-butadiene. In embodiments of the invention, rectifier column 102 can be configured to use 1,3-butadiene to strip butenes from the solvent into top stream 14. At least a portion of top stream 14 is recycled back to main washer column 101. In embodiments of the invention, rectifier column 102 includes a distillation column. In embodiments of the invention, rectifier column 102 is further configured to produce first side stream 16 comprising primarily 1,3-butadiene and some acetylenes.

According to embodiments of the invention, a side outlet of rectifier column 102 is in fluid communication with after washer column 103 such that first side stream 16 flows from rectifier column 102 to after washer column 103. After washer column 103 may be configured to separate first side stream 16 to form crude 1,3-butadiene stream 17 comprising primarily 1,3-butadiene and after washer bottom stream 18 comprising primarily the solvent and acetylenes. In embodiments of the invention, after washer column 103 includes an extractive distillation column with fresh solvent stream 82 being fed from the top. After washer bottom stream 18 may be flowed to rectifier column 102. In embodiments of the invention, a top outlet of after washer column 103 is in fluid communication with propyne distillation column 107, which is configured to separate crude 1,3-butadiene stream 17 to produce a propyne stream 30 comprising dilute propyne and second crude 1,3-butadiene stream 57. A bottom outlet of propyne column 107 may be in fluid communication with 1,3-butadiene refining column 106, which is configured to produce 1,3-butadiene product stream 31 comprising primarily 1,3-butadiene. 1,3-butadiene product stream 31 may comprise more than 99.5 wt. % 1,3-butadiene. In embodiments of the invention, 13,-butadiene product stream further comprises hydrocarbons that are heavier than 1,3-butadiene.

In embodiments of the invention, system 100 comprises two or more heat exchange units configured to heat bottom stream 15, and a flash drum downstream to each heat exchange unit configured to remove some $C_4$ hydrocarbons from bottom stream 15. In embodiments of the invention, first heat exchange unit 201 is in fluid communication with a bottom outlet of rectifier 102. First heat exchange unit 201 may comprise two or three heat exchangers in series configured to heat bottom stream 15 to form first heated bottom stream 35. According to embodiments of the invention, system 100 further includes first flash drum 110 in fluid communication with an outlet of first heat exchange unit 201 such that first heated bottom stream 35 flows from first heat exchange unit 201 to first flash drum 110. First flash drum 110 is configured to produce, via flash-evaporation, first vapor stream 41 comprising primarily $C_4$ hydrocarbons, and first degassed bottom stream 51 comprising the solvent and some $C_4$ hydrocarbons. System 100 may further comprise second heat exchange unit 202 in fluid communication with an outlet of first flash drum 110 such that first degassed bottom stream 51 flows to second heat exchange unit 202. Second heat exchange unit 202 is configured to heat first degassed bottom stream 51 to form second heated bottom stream 36. System 100 may include second flash drum 120 in fluid communication with an outlet of second heat exchange unit 202 such that second heated bottom stream 36 flows to second flash drum 120. Second flash drum 120 can be configured to produce, via flash-evaporating, second vapor stream 42 comprising primarily $C_4$ hydrocarbons, and second degassed bottom stream 52 comprising the solvent and some $C_4$ hydrocarbons. In embodiments of the invention, system 100 further includes third heat exchange unit 203 configured to heat second degassed bottom stream 52 to produce third heated bottom stream 37. System 100 may further comprise third flash drum 130 configured to flash evaporate third heated bottom stream 37 to produce third vapor stream 43 comprising primarily $C_4$ hydrocarbons, and third degassed bottom stream 53 comprising the solvent and some $C_4$ hydrocarbons.

First vapor stream 41, second vapor stream 42, and/or third vapor stream 43 may be flowed back to rectifier column 102. Third heat exchange unit 203 may be operated with steam as a heating medium. The steam can be low pressure steam. In embodiments of the invention, first flash drum 110 may be disposed outside of rectifier column 102 or in a compartment located inside of the bottom of rectifier column 102. In embodiments of the invention, first heat exchange unit 201, second heat exchange unit 202, and third heat exchange unit 203 each individually comprises a recompression pump configured to keep the liquid pressure after being heated in liquid phase.

In embodiments of the invention, system 100 further comprises fourth heat exchange unit 204 in fluid communication with an outlet of third flash drum 130. Fourth heat exchange unit 204 may be configured to cool third degassed liquid stream 53 to produce cooled degasser feed stream 54. According to embodiments of the invention, system 100 further comprises degasser column 104 configured to separate cooled liquid stream 54 to form first hot lean solvent stream 19 comprising primarily the solvent, and second side stream 20 comprising $C_4$ acetylenes. First hot lean solvent stream 19 may include less than 0.001 wt. % hydrocarbons. Second side stream 20 may comprise less than 30 wt. % acetylene, preferably 10 to 20 wt. %. Second side stream 20 may further include water vapor and/or 1,3-butadiene. A side outlet of degasser column 104 is in fluid communication with acetylene washer 140 such that second side stream 20 flows from degasser column 104 to acetylene washer 140. Acetylene washer 140 may be configured to recover acetylene from second side stream 20.

In embodiments of the invention, degasser column 104 is configured to further produce third overhead stream 21 comprising $C_4$ hydrocarbons. Degasser column 104 may include a distillation column. Degasser column 104 may further include a cooling column and/or a cooling heat exchanger. A top outlet of degasser column 104 may be in fluid communication with compressor 150, which is configured to compress third overhead stream 21 to form compressed recycle stream 22. In embodiments of the invention, an outlet of compressor 150 is in fluid communication with an inlet of rectifier column 102 such that compressed recycle stream 22 flows to rectifier column 102.

The degasser overhead vapor flow (third overhead stream 21) may be at about 1.5 bar, comprising primarily 1,3-butadiene and some impurities of water vapor, the solvent, and some hydrocarbons. According to embodiments of the invention, as shown in FIG. 1D, system 100 includes water cooler 151 in fluid communication with an top outlet of degasser column 104 such that third overhead stream 21 can be cooled to form cooled third overhead stream 21a. Cooled third overhead stream 21a may be at a temperature of about 42° C. In embodiments of the invention, cooled third overhead stream 21a includes about 95 vol. % vapor. According to embodiments of the invention, an outlet of water cooler 151 may be in fluid communication with an overhead flash drum 152 such that cooled third overhead stream 21a can be separated to form vapor stream 21b and liquid stream 21c. Vapor stream 21b can be compressed by compressor 150 and both compressed vapor stream and liquid stream 21c can be sent to rectifier column 102.

Figure 1B:
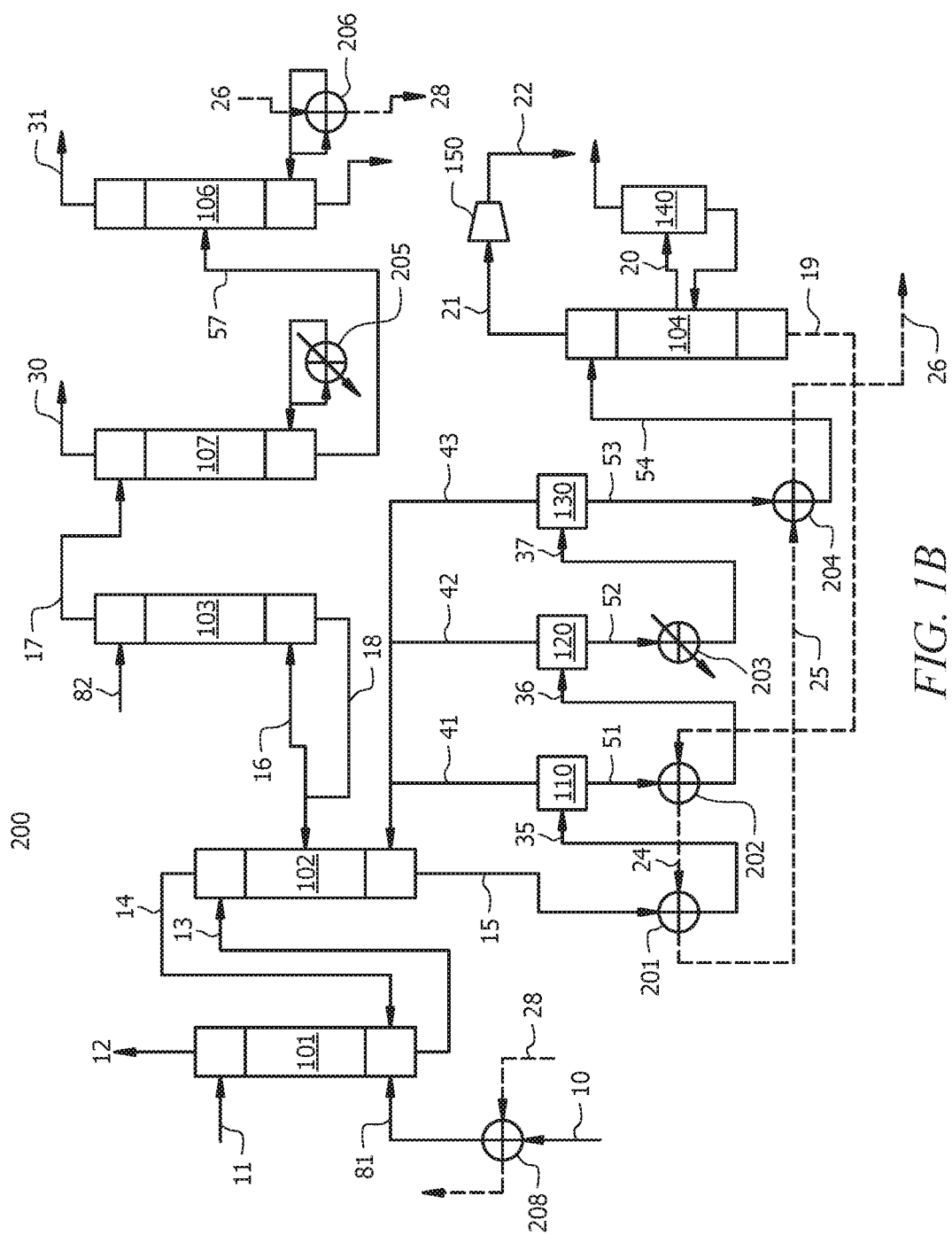
Figure 1C:
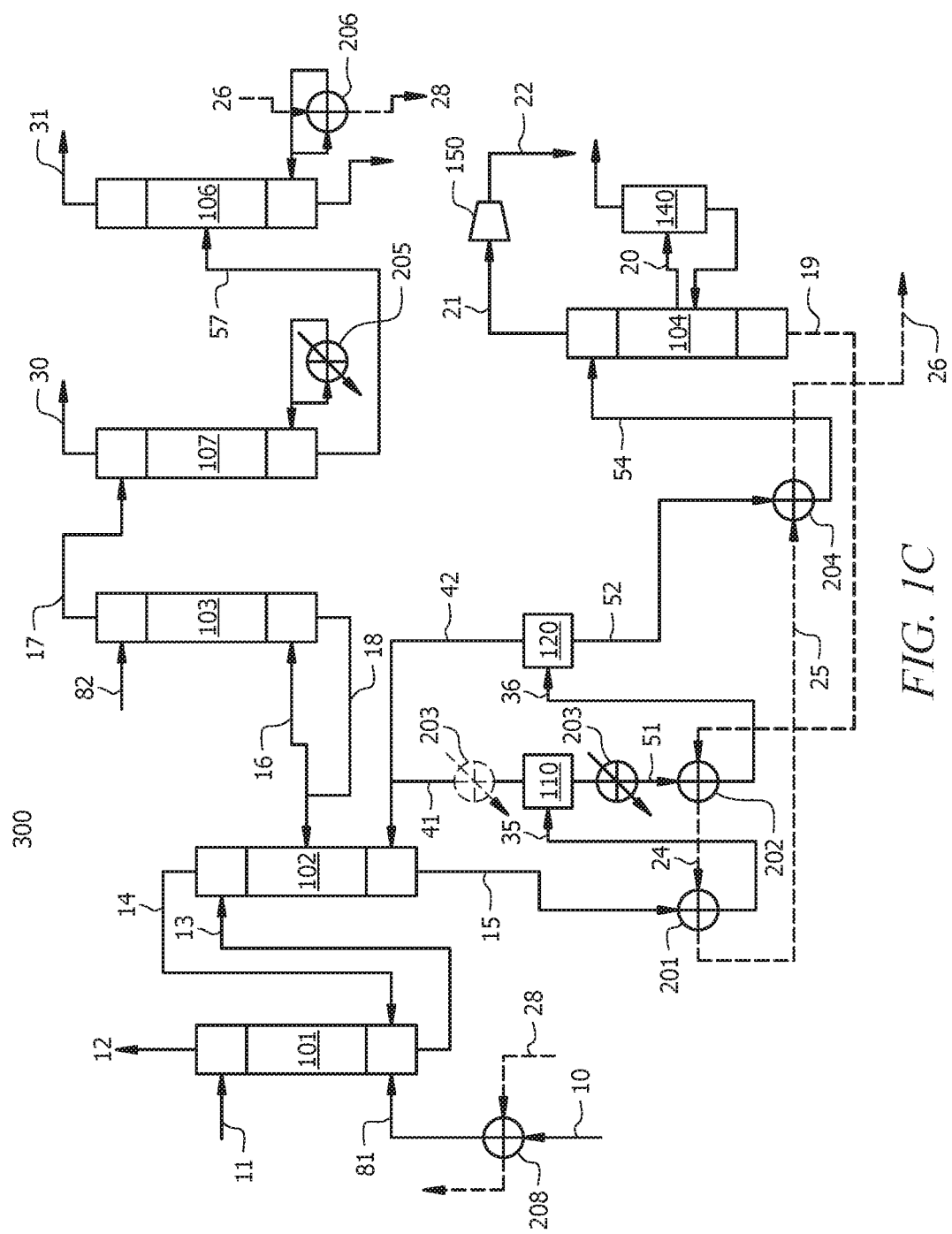
Figure 1D:
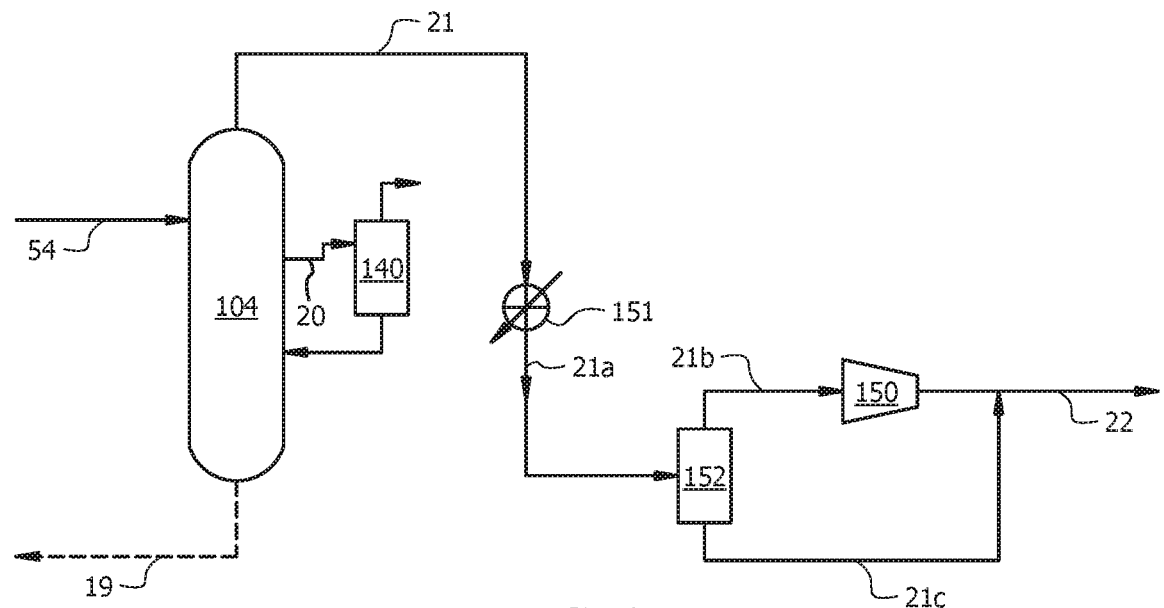
FIGS. 1D and 1E show schematic diagrams of systems for compressing an overhead stream from a degasser column, according to embodiments of the invention.
Figure 1E:
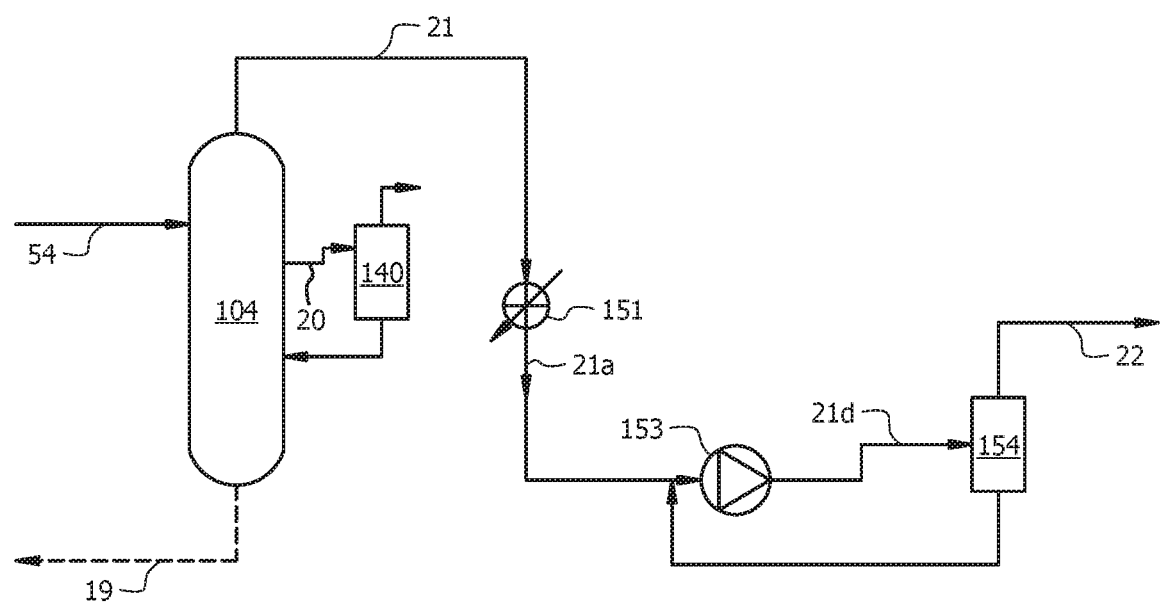

As shown in FIG. 1E, system 100 can include multiphase pump 153, which replaces compressor 150 shown in FIG. 1D. In embodiments of the invention, an outlet of water cooler 151 may be in fluid communication with multiphase pump 153 such that cooled third overhead stream 21a flows to multiphase pump 153. Multiphase pump 153 is configured to pump cooled third overhead stream 21a to form compressed cooled overhead stream 21d, which is optionally flowed into liquid vessel 154. Compressed cooled overhead stream 21d may be at a pressure of about 5.3 bar. In embodiments of the invention, a portion of liquid in liquid vessel 154 is flowed back to an inlet of multiphase pump 153 to adjust liquid ratio in multiphase pump 153. Another portion of liquid in liquid vessel 154 is flowed to rectifier column 102 as compressed recycle stream 22. According to embodiments of the invention, multiphase pump 153 can be configured to generate an internal liquid recycle portion for adjusting the vapor volume fraction at an outlet thereof, and the outlet of multiphase pump 153 is in fluid communication with an inlet of rectifier column 102 such that at least a portion of compressed cooled overhead stream 21d is directly flowed back to rectifier column 102. Multiphase pump The use of multiphase pump 153 in system 100 has been facilitated by the lower volume flow rate of third overhead stream 21 from degasser column 104. It is contemplated in the context of the disclosure that this feature can also be applied to other butadiene extraction technologies using other solvents with different configurations containing a compressor, and the solvent includes dimethyl formamide, acetonitrile, or a combination (or mixture) with other solvents.

In embodiments of the invention, first hot lean solvent stream 19 flows through second heat exchange unit 202 as a heating medium to form second hot lean solvent stream 24. Second hot lean solvent stream 24 flows through first heat exchange unit 201 as a heating medium to form cooled lean solvent stream 25. Cooled lean solvent stream 25 flows through fourth heat exchange unit 204 as a cooling medium to form heated lean solvent stream 26. In embodiments of the invention, system 100 comprises seventh heat exchange unit 207 configured to cool heated lean solvent stream 26 to form second cooled lean solvent stream 27. Second cooled lean solvent stream 27 can be flowed through a reboiler (including fifth heat exchange unit 205) of propyne column 107 to form third cooled lean solvent stream 27' and/or through a reboiler (including sixth heat exchange unit 206) of 1,3-butadiene refining column 106 as a heating medium to form fourth cooled lean solvent stream 28. Fourth cooled solvent stream 28 can be used as a cooling medium for heated lean solvent stream 26 in seventh heat exchange unit 207 to form second heated lean solvent stream 29. According to embodiments of the invention, system 100 includes feed vaporizer 208 configured to vaporize $C_4$ hydrocarbon mixture stream 10 to form $C_4$ hydrocarbon feed stream 81. Second heated lean solvent stream 29 can be used as a heating medium for feed vaporizer 208.

Alternatively, as shown in FIG. 1B, system 200 includes all the elements and units of system 100 except system 200 does not include seventh heat exchange unit 207 and the reboiler of propyne column 107 (including fifth heat exchange unit 205) uses low temperature steam condensate as a heating medium. In system 200, heated lean solvent stream 26 can flow through sixth heat exchange unit 206 as a heating medium to form fourth cooled lean solvent stream 28. Fourth cooled lean solvent stream 28 can be used as a heating medium for feed vaporizer 208.

As shown in FIG. 1C, system 300 includes all the elements and units of system 200 except that system 300 does not third flash drum 130. Third heat exchanger 203, however, is located either just before or after second heat exchanger 202 configured to boost the degassed solvent temperature before feeding it to flash drum 120.] Second degassed bottom stream 52 can be cooled in fourth heat exchange unit 204 to form cooled degasser feed stream 54.

B. Method of Separating $C_4$ Hydrocarbon Mixture

Figure 2:
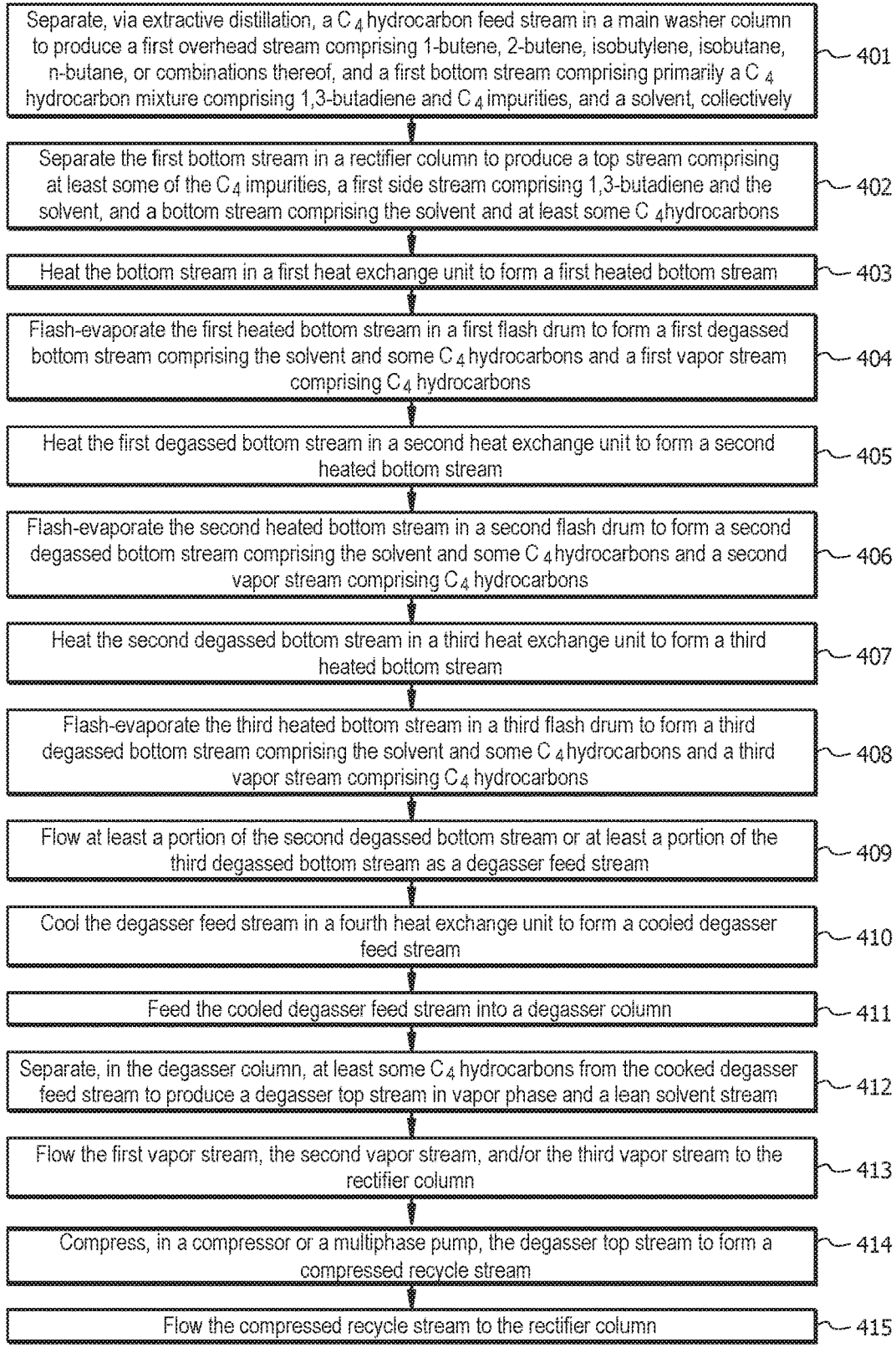
FIG. 2 shows a schematic flowchart of a system for separating 1,3-butadiene from a mixture of $C_4$ hydrocarbons, according to embodiments of the invention.

Methods for separating $C_4$ hydrocarbon mixture have been discovered. As shown in FIG. 2, embodiments of the invention include method 400 for separating a mixture of $C_4$ hydrocarbons with improved efficiency and reduced energy consumption compared to conventional $C_4$ separation methods. Therefore, method 400 can be used for solvent recovery during separation of 1,3-butadiene from a $C_4$ mixture with improved efficiency and reduced production cost compared to conventional methods. Method 400 may be implemented by systems 100, 200, and/or 300, as shown in FIGS. 1A-1C and described above.

According to embodiments of the invention, as shown in block 401, method 400 includes separating, via extractive distillation, $C_4$ hydrocarbon feed stream 81 in main washer column 101 to produce first overhead stream 12 comprising 1-butene, 2-butene, isobutylene, isobutane, n-butane, cis and trans butene isomers, or combinations thereof and first bottom stream 13 comprising a mixture of $C_4$ hydrocarbons and a solvent. In embodiments of the invention, the $C_4$ hydrocarbons of the first bottom stream 13 comprise 1,3-butadiene, 1,2-butadiene, 1-butene, 2-butene, isobutylene, isobutane, n-butane, cis and trans butene isomers, or combinations thereof. $C_4$ hydrocarbons of first bottom stream 13 may further comprise acetylene, propyne, $C_5$ hydrocarbons, or combinations thereof. The solvent may include N-Methyl-1-2-Pyrrolidone (NMP). The solvent may further comprise 8-10 wt. % water, preferably about 8.3 wt. % water. In embodiments of the invention, main washer column 101 is operated at an overhead boiling temperature range of 39 to 45° C., a bottom temperature range of 58 to 65° C., and an operating pressure of 4.2 to 5 bar. Main washer column 101 may be operated at a solvent to feed ratio (volumetric ratio of first solvent stream 11 to $C_4$ hydrocarbon feed stream 81) in a range of 8 to 12 and all ranges and values there between.

According to embodiments of the invention, as shown in block 402, method 400 includes separating first bottom stream 13 including the mixture of $C_4$ hydrocarbons and the solvent in rectifier column 102 to produce top stream 14 comprising at least some of the $C_4$ hydrocarbons and bottom stream 15 comprising (a) primarily the solvent and (b) at least some $C_4$ hydrocarbons. In embodiments of the invention, rectifier column 102 is operated at an overhead boiling temperature range of 60 to 65° C., and an operating pressure of 4.9 to 5.3 bar. Bottom stream 15 may be at a temperature of 70 to 75° C., preferably 72° C., and a pressure of 5.0 to 5.5 bar, preferably 5.1 bar. In embodiments of the invention, separating at block 402 further produces first side stream 16 comprising mainly 1,3-butadiene and other $C_4$ hydrocarbons.

According to embodiments of the invention, as shown in block 403, method 400 includes heating bottom stream 15 in first heat exchange unit 201, which may comprise two to three heat exchangers in series, to form first heated bottom stream 35. First heated bottom stream 35 may be at a first temperature of 100 to 110° C., preferably 105° C. and all ranges and values there between. At block 403, bottom stream 15 is heated using second hot lean solvent stream 24 as a heating medium in first heat exchange unit 201 and form cooled lean solvent stream 25. Cooled lean solvent stream 25 may be at a temperature of 79 to 86° C., preferably 83° C. According to embodiments of the invention, as shown in block 404, method 400 includes flash-evaporating first heated bottom stream 35 in first flash drum 110 to form first degassed bottom stream 51 comprising the solvent and some $C_4$ hydrocarbons and first vapor stream 41 comprising primarily $C_4$ hydrocarbons. In embodiments of the invention, flash-evaporating in first flash drum 110 at block 404 is conducted at a first pressure of 4.9 to 5.4 bar and all ranges and values there between. First degassed bottom stream 51 may comprise about 50% less hydrocarbons than that of bottom stream 15. First degassed bottom stream may be at a temperature of 90 to 100° C.

According to embodiments of the invention, as shown in block 405, method 400 includes heating first degassed bottom stream 51 in second heat exchange unit 202 to form second heated bottom stream 36. Second heated bottom stream 36 may be at a second temperature of 115 to 125° C., preferably 120° C. At block 405, first degassed bottom stream 51 can be heated using first hot lean solvent stream 19 as a heating medium in second heat exchange unit 102 to form second hot lean solvent stream 24. According to embodiments of the invention, as shown in block 406, method 400 includes flash-evaporating second heated bottom stream 36 in second flash drum 120 to form second degassed bottom stream 52 comprising the solvent and some $C_4$ hydrocarbons and second vapor stream 42 comprising primarily $C_4$ hydrocarbons. In embodiments of the invention, flash-evaporating at block 406 is conducted at a second pressure of 5.0 to 5.4 bar and all ranges and values there between. Second degassed bottom stream 52 may contain about a third of hydrocarbons of bottom stream 15.

According to embodiments of the invention, as shown in block 407, method 400 includes optionally heating second degassed bottom stream 52 in third heat exchange unit 203 to form third heated bottom stream 37. Third heated bottom stream may be at a third temperature of 120 to 130° C., preferably 125° C. Third heat exchange unit 203 may be operated with a low pressure steam as a heating medium. According to embodiments of the invention, as shown in block 408, method 400 includes optionally flash-evaporating third heated bottom stream 37 in third flash drum 130 to form third degassed bottom stream 53 comprising the solvent and some $C_4$ hydrocarbons and third vapor stream 43 comprising primarily $C_4$ hydrocarbons. In embodiments of the invention, flash-evaporating at block 408 is conducted at a third pressure of 5.0 to 5.4 bar and all ranges and values there between.

According to embodiments of the invention, as shown in block 409, method 400 includes flowing second degassed bottom stream 52 or third degassed bottom stream 53 as a degasser feed stream to degasser column 104. Third degassed bottom stream 53 may include about one-third of hydrocarbons of bottom stream 15. Third degassed bottom stream may be at a temperature of 118 to 128° C., preferably 123° C. Method 400 may further include cooling the degasser feed stream in fourth heat exchange unit 204 to form cooled degasser feed stream 54, as shown in block 410. In embodiments of the invention, cooled degasser feed stream 54 is at a degasser feed temperature of 100 to 110° C., preferably 102° C. and all ranges and values there between.

According to embodiments of the invention, as shown in block 411, method 400 includes feeding cooled degasser feed stream 54 into degasser column 104. As shown in block 412, method 400 includes separating, in degasser column 104, $C_4$ hydrocarbons from cooled degasser feed stream 54 to produce third overhead stream 21 comprising $C_4$ hydrocarbons in vapor phase, and first hot lean solvent stream 19 comprising primarily the solvent. In embodiments of the invention, first hot lean solvent stream 19 comprises less than 0.001 wt. % $C_4$ hydrocarbons. First hot lean solvent stream 19 may be at a temperature of about 150° C. At block 412, degasser column 104 may be operated at an overhead boiling temperature range of 90 to 110° C., and an operating pressure of 1.45 to 1.65 bar. First hot lean solvent stream 19 may be at a temperature about 150° C. In embodiments of the invention, separating at block 412 further produces second side stream 20 comprising about less than 30 wt. %, preferably 10 to 20 wt. % acetylene and the solvent. Second side stream 20 may further include water vapor, 1,3-butaidene. Second side stream 20 may be further processed in acetylene washer 140 to recover acetylene. According to embodiments of the invention, as shown in block 413, method 400 includes flowing first vapor stream 41, second vapor stream 42, and/or third vapor stream 43 to rectifier column 102.

According to embodiments of the invention, as shown in block 414, method 400 includes compressing third overhead stream 21 to form a compressed recycle stream 22. Compressing at block 414 may be conducted using compressor 150 and/or multiphase pump 154. Compressed recycle stream 22 is at a pressure of 5 to 5.6 bar and all ranges and values there between including 5.1 bar, 5.2 bar, 5.3 bar, 5.4 bar, and 5.5 bar. As shown in block 415, method 400 may include flowing compressed recycle stream 22 to rectifier column 102.

In embodiments of the invention, first side stream 16 from rectifier column 102 is further processed via extractive distillation in after washer column 103 to produce crude 1,3-butadiene stream 17 comprising 96 to 99 wt. % 1,3-butadiene. In embodiments of the invention, after washer column 103 is operated at an overhead boiling temperature range of 39 to 45° C., a bottom temperature range of 63 to 68° C., and an operating pressure of 4.7 to 5.1 bar. After washer column 103 may be operated at a solvent to feed ratio (volumetric ratio of second solvent stream 82 to first side stream 16) in a range of 1 to 4 and all ranges and values there between. According to embodiments of the invention, crude 1,3-butadiene stream 17 is further processed in propyne column 107 to produce propyne stream 30 comprising 10 to 50 wt. % propyne and second crude 1,3-butadiene stream 17 comprising 1,3-butadiene. In embodiments of the invention, propyne column 107 is operated at an overhead boiling temperature range of 45 to 55° C., a bottom temperature range of 53 to 61° C., and an operating pressure of 6 to 7 bar. Second 1,3-butadiene stream 57 may be further processed in 1,3-butadiene refining column 106 to produce product stream 31 comprising primarily 1,3-butadiene. Product stream 31 may comprise 99.5 to 99.8 wt. % 1,3-butadiene. In embodiments of the invention, 1,3-butadiene refining column 106 is operated at an overhead boiling temperature range of 36 to 45° C., a bottom temperature range of 45 to 54° C., and an operating pressure of 4.0 to 5.0 bar.

In embodiments of the invention, first hot lean solvent stream 19 is sequentially flowed through first heat exchange unit 20 and second heat exchange unit 202 as a heating medium to form cooled lean solvent stream 25. Cooled lean solvent stream 25 may be at a temperature of 80 to 88° C. Cooled lean solvent stream 25 may be used as a cooling medium in fourth heat exchange unit 204 to form heated lean solvent stream 26. Heated lean solvent stream 26 may be at a temperature of 100 to 120° C. Heated lean solvent stream 26 can be cooled in seventh heat exchange unit 207 to form second cooled lean solvent stream 27 at a temperature range of 100 to 90° C. Second cooled lean solvent stream 27 may be sequentially flowed as a heating medium in fifth heat exchange unit 205 for providing heat to the reboiler of propyne column 107, and sixth heat exchange unit 206 for providing heat to the reboiler of 1,3-butadiene refining column 106 and form fourth cooled lean solvent stream 28. In embodiments of the invention, fourth cooled lean solvent stream 28 can be used as a cooling medium in seventh heat exchange unit 207 to form second heated lean solvent stream 29. Second heated lean solvent stream 29 can be used as a heating medium in feed vaporizer 208 for vaporizing $C_4$ hydrocarbon mixture stream 10. Second heated lean solvent stream 29 may be at a temperature of 71 to 79° C.

Although embodiments of the present invention have been described with reference to blocks of FIG. 2 it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLE 1

Simulations on Solvent Recovery Process Used in 1,3-butadiene Production

Simulations of solvent recovery process for 1,3-butadiene production were performed in PROII software platform. The simulation results obtained for a conventional system of the prior art that has one flash-evaporating step for rich solvent stream (the bottom stream from the rectifier column) were compared with the simulation results obtained for systems shown in FIGS. 1A-1C. All simulation runs were conducted using the same feed composition and feed conditions. The first heat exchange unit used in each system is substantially the same. The second heat exchange unit used in systems shown in FIGS. 1A-1C is substantially the same, and the third heat exchange unit used in systems shown in FIGS. 1A and 1B is substantially the same. The results are shown in Table 1. The simulation results for the systems shown in FIGS. 1A-1C are also further compared in the discussion herein with another system performance disclosed in U.S. Pat. No. 9,296,667 B2 which is considered as an improvement to the conventional system of prior art in terms of reducing degassed hydrocarbons in the solvent.

greatly reduces the potential fouling in heat exchangers. The lean solvent (the bottom stream from the degasser column) at 150° C. was used to heat a partially degassed solvent in the second heat exchange unit with about 50% less hydrocarbons than in the original feed, which again reduces the fouling potential in this heat exchange unit that was exposed to hot stream. This is also in contrast with conventional system where only one third reduction in the rich solvent was achieved from rectifier column reboiler which was exposed to hot lean solvent of 175° C.

In addition, the final percentage of evaporated hydrocarbons is in a range of from 68% up to 74% compared to 60% for the conventional system. The highest degassing value of 74% is also comparable with the value disclosed in U.S. Pat. No. 9,296,667 B2. Therefore, the current invention can achieve a comparable degassing efficiency but at lower heating temperature of 125° C. of the rich solvent compared to 138° C. for the process disclosed in U.S. Pat. No. 9,296,667 B2. Further to this point the dissolved gas in the third heat exchange unit was reduced by two thirds (5.6 versus 17.3) against one third reduction disclosed in U.S. Pat. No. 9,296,667 B2. Thus, mild heating in the systems of FIGS. 1A to 1C can reach same efficiency with three flashes in this invention as disclosed in in U.S. Pat. No. 9,296,667

TABLE 1

Simulation results

| Parameter | Conventional system | System shown in FIG. 1C | System shown in FIG. 1B | System shown in FIG. 1A |
|---|---|---|---|---|
| Dissolved gas % in the first heat exchange unit against inlet temperature of lean solvent stream and outlet temperature of rich solvent | 17%/150° C. | 17.5%/123° C. | 17.5%/123° C. | 17.3%/123° C. |
| Outlet temperature of heated rich solvent from first heat exchange unit | 120° C. | 105° C. | 105° C. | 105° C. |
| Dissolved gas % in rich solvent in the second heat exchange unit and inlet temperature of lean solvent stream | — | 9.3%/150° C. | 9.3%/150° C. | 9.3%/150° C. |
| Dissolved gas % in solvent in the third heat exchange unit and inlet temperature of steam | — | — | 5.7%/133° C. | 5.6%/133° C. |
| Outlet temperature of heated rich solvent from the third heat exchange unit. | — | — | 118° C. | 125° C. |
| Total hydrocarbon degassed from rich solvent feed (bottom stream from the rectifier column) % | 60% | 68% | 71% | 74% |
| Duty of the compressor (KW) for compressing degasser top stream and its % compared to the conventional system | (1622)/100% | 80.4% | 74.4% | 62.1% |
| Electric duty of all solvent recompression pumps of the first, second, and third exchange units plus compressor duty (KW) as % compared to the conventional system | (2351)/100% | 87.8% | 89.1% | 93.5% |
| Compressor cooling water duty (KW) as % compared to the conventional system | (3757)/100% | 76% | 72% | 62% |

As shown in Table 1, the rich solvent (bottom stream from the rectifier column) was heated to a moderate temperature of 105° C. against lower temperature of lean solvent of 123° C. than the 150° C. of the conventional system, which B2, which discloses higher heating with richer solvent in hydrocarbons using two flash-evaporating steps.

The compressor duty of the new configuration was progressively reduced by almost 38% more than the duty of the conventional system operated at the same low degasser pressure. However, the multi-flash evaporation steps of this invention require recompression of the rich solvent after every flash to keep it in liquid phase before reheating for the next flash, and therefore the duties of intermediate excess re-pumping required are computed. As shown the total duties of compressor with additional extra pumping duties, there is a net saving in duty by about 8% to 12% compared to the conventional system and therefore the net electrical load required is less for the systems shown in FIGS. 1A to 1C. Additionally, the compressor cooler duty was also reduced by about 26% to 38% compared to the conventional system.

EXAMPLE 2

Simulation of Overhead Conditions for Degasser Column

The following example illustrates yet another feature of the current invention. Following from the cases shown above, Table 2 shows the degasser overhead stream conditions. The cases illustrate that the degasser pressure considered in this invention is based on low overhead pressure and temperature in all cases are similar to the conventional system. Low degasser pressure is reflected in low temperature processing which is preferable for butadiene technology. The table shows that the volumetric flow of the overhead is greatly reduced due to the multi-flash concept (i.e., two or more heating-degassing cycles before the bottom stream from the rectifier column is flowed into the degasser column) adopted in this invention. The degasser overhead was first cooled in a condenser to about 42° C. with cooling water. Following the condenser as depicted in FIG. 1D, the cooled stream contained gas and liquid mixture with a gas vapor fraction (GVF) is shown in the table. In all the cases it was found that it was nearly constant. The liquid is mostly water with water, some hydrocarbons, and NMP solvent as impurities.

In the oil and gas industry there has been recent usage of a multi-phase pump concept that can handle gas fraction up to 0.97 in liquids and pump it to high pressures. As shown in Table 2, the gas fraction was within the limits of such pumps. The reduced flow rate of the current invention can also be handled by one of such pumps. It is therefore claimed as another feature of this invention that a compressor can be replaced by a multi-phase pump where a degasser overhead vapor is cooled by a condenser and the flow is fed to a multiphase pump to raise the pressure from 1.5 bar to slightly above rectifier pressure of 5.3 bar. A liquid vessel is used in order to supply a small liquid stream back to the inlet feed such that a desired vapor fraction is maintained throughout operation. Or the desired vapor fraction can be regulated or maintained by a liquid recycle stream within the multiphase pump.

The use of a multiphase pump instead of a compressor has many advantages. The cost is much cheaper, the duty is much less and operation-wise it does not suffer from tripping as sometimes happen with compressors when upstream pressure varies, which can lead to shutting down the whole plant as there is usually no standby compressor because of its high cost. Whereas by using a pump, a second standby pump is the usual engineering practice that is still cheaper than one compressor, so there is no interruption to plant operation. The use of such a multiphase pump allows the degasser to operate at its low pressure. This is in contrast to U.S. Pat. No. 9,296,667 B2 where the degasser pressure and temperature was raised in order for the compressor flow to decrease and therefore a cheaper liquid ring compressor can be used.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of separating a mixture comprising (1) $C_4$ hydrocarbons and (2) a solvent, the method comprising:
separating the mixture in a rectifier column to produce a top stream comprising at least some $C_4$ hydrocarbons and a bottom stream comprising (a) primarily the solvent and (b) at least some $C_4$ hydrocarbons;
heating the bottom stream in a first heat exchange unit to form a first heated bottom stream at a first temperature;
flash-evaporating the first heated bottom stream to separate at least some $C_4$ hydrocarbons from the first heated bottom stream to form a first degassed bottom stream;
heating the first degassed bottom stream in a second heat exchange unit to form a second heated bottom stream at a second temperature;
flash-evaporating the second heated bottom stream to separate at least some $C_4$ hydrocarbons from the second heated bottom stream to form a second degassed bottom stream;

TABLE 2

Overhead conditions for degasser column

| Parameter | Conventional system | System shown in FIG. 1C | System shown in FIG. 1B | System shown in FIG. 1A |
|---|---|---|---|---|
| Degasser Overhead pressure bar and temp ° C. | 1.5/95 | 1.5/95 | 1.5/95 | 1.5/95 |
| Degasser overhead flow (m³/h) as % to conventional system | 94/100 | 77 | 73 | 63 |
| Degasser GVF after cooling | 0.95 | 0.95 | 0.95 | 0.95 | feeding at least a portion of the second degassed bottom stream as a degasser feed stream to a degasser column to further remove $C_4$ hydrocarbons from the solvent; and removing at least some $C_4$ hydrocarbons from the degasser feed stream in the degasser column to produce a degasser top stream comprising the $C_4$ hydrocarbons in vapor phase, and a first hot lean solvent stream comprising primarily the solvent.

2. The method of claim 1, further comprising:
prior to the step of flash-evaporating the second heated bottom stream, heating the first degassed bottom stream in an additional heat exchange unit installed up stream or downstream to the second heat exchange unit.

3. The method of claim 2, wherein the additional heat exchange unit is operated with a low pressure steam as a heating medium.

4. The method of claim 1, further comprising:
compressing the degasser top stream to form a compressed recycle stream; and
flowing the compressed recycle stream to the rectifier column.

5. The method of claim 4, wherein the compressing is conducted using a compressor or a multiphase pump.

6. The method of claim 1, further comprising:
prior to the feeding step, heating the second degassed bottom stream in a third heat exchange unit to form a third heated bottom stream at a third temperature;
flash-evaporating the third heated bottom stream to separate at least some $C_4$ hydrocarbons from the third heated bottom stream to form a third degassed bottom stream; and
feeding the third degassed bottom stream as a degasser feed stream to the degasser column configured to further remove $C_4$ hydrocarbons from the solvent.

7. The method of claim 6, wherein the third exchange unit is operated using low pressure steam as a heating medium.

8. The method of claim 6, wherein the flash-evaporating of the third heated bottom stream further produces a third vapor stream comprising primarily the $C_4$ hydrocarbons, and the method further comprises flowing the third vapor stream to the rectifier column.

9. The method of claim 1, wherein the first hot lean solvent stream is flowed into the first heat exchange unit and/or the second heat exchange unit as a heating medium to form a second hot lean solvent stream.

10. The method of claim 9, further comprising: prior to feeding the degasser feed stream to the degasser, cooling, in a fourth heat exchanger, the degasser feed stream with the cooled lean solvent stream as a cooling medium to form a cooled degasser feed stream and a heated lean solvent stream.

11. The method of claim 10, wherein the heated lean solvent stream is used as a heating medium to heat a reboiler of a 1,3-butadiene refining column configured to purify a crude 1,3-butadiene stream, and optionally a reboiler of a propyne refining column configured to separate propyne from a hydrocarbon mixture.

12. The method of claim 11, wherein the heated lean solvent stream is used as a heating medium to heat the reboiler of the propyne refining column and the reboiler of the 1,3-butadiene refining column in series.

13. The method of claim 10, wherein the heated lean solvent stream is used as a heating medium to heat a reboiler of a 1,3-butadiene refining column and a feed vaporizer configured to vaporize $C_4$ hydrocarbon feed for an extractive distillation column.

14. The method of claim 13, wherein the extractive distillation column is configured to separate the vaporized $C_4$ hydrocarbon feed to produce the mixture of $C_4$ hydrocarbons.

15. The method of claim 1, wherein the flash-evaporating of the first heated bottom stream further produces a first vapor stream comprising primarily the $C_4$ hydrocarbons, and the flash-evaporating of the second heated bottom stream further produces a second vapor stream comprising primarily the $C_4$ hydrocarbons, wherein the first vapor stream and the second vapor stream are flowed to the rectifier column.

16. The method of claim 1, wherein the $C_4$ hydrocarbons comprise 1-butene, 2-butene, n-butane, isobutane, isobutene, 1,3-butadiene, 1,2-butadiene, cis and trans butene isomers, $C_4$ acetylenes, propyne, or combinations thereof.

17. The method of claim 1, wherein the removing at least some $C_4$ hydrocarbons from the degasser feed stream further produces a side stream comprising $C_4$ acetylene.

18. The method of claim 17, wherein the side stream is further separated in an acetylene washer column to produce an acetylene stream comprising less than 30 wt. % $C_4$ acetylene.

19. The method of claim 1, wherein the solvent comprises n-methyl-2-pyrrolidone, dimethyl formamide, or acetonitrile.

20. The method of claim 1, wherein the first hot lean solvent stream comprises less than 0.01 wt. % $C_4$ hydrocarbons.

* * * * *